US00PP24712P2

(12) United States Plant Patent
Hanes

(10) Patent No.: US PP24,712 P2
(45) Date of Patent: Jul. 29, 2014

(54) ***PELARGONIUM* PLANT NAMED 'PEQZ0004'**

(50) Latin Name: ***Pelargonium* spp.**
Varietal Denomination: PEQZ0004

(75) Inventor: Mitchell Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 95 days.

(21) Appl. No.: 13/507,816

(22) Filed: Jul. 31, 2012

(51) Int. Cl.
*A01H 5/00* (2006.01)

(52) U.S. Cl.
USPC ..... Plt./324

(58) Field of Classification Search
USPC ..... Plt./324, 329, 330
See application file for complete search history.

(56) References Cited

U.S. PATENT DOCUMENTS

PP20,245 P2 * 9/2009 Hanes ..... Plt./324

* cited by examiner

*Primary Examiner* — Susan McCormick Ewoldt
(74) *Attorney, Agent, or Firm* — Joshua L. Price

(57) ABSTRACT

A new *Pelargonium* plant named 'PEQZ0004' particularly distinguished by the has large semi-double deep red inflorescences with a more blue hue, good garden performance growing well in sun and shade, lateral plant habit, excellent branching and a foliage that resembles in shape the foliage of *Pelargonium×hortorum* varieties.

1 Drawing Sheet

Latin name of the genus and species of the plant claimed: *Pelargonium* spp.

Varietal denomination: 'PEQZ0004'.

BACKGROUND OF THE NEW PLANT

The present invention comprises a new *Pelargonium*, botanically known as *Pelargonium* spp., and hereinafter referred to by the variety name 'PEQZ0004'.

'PEQZ0004' is a product of a planned breeding program. The new cultivar 'PEQZ0004' has large semi-double deep red inflorescences with a more blue hue, good garden performance growing well in sun and shade, lateral plant habit, excellent branching and a foliage that resembles in shape the foliage of *Pelargonium×hortorum* varieties.

'PEQZ0004' originates from a hybridization in a controlled breeding program in November 2007 in Gilroy, Calif. The female parent was a proprietary interspecific plant identified as 'Amri Trared', U.S. Plant Pat. No. 20,245, with dark red color, somewhat larger flowers, and larger plant habit when compared to 'PEQZ0004'.

The male parent of 'PEQZ0004' was an unpatented, proprietary plant identified as '10622-1' with blue rose flowers and fewer branches when compared to 'PEQZ0004'. The resultant seed was sown in April 2008 in Gilroy, Calif.

'PEQZ0004' was selected as one flowering plant within the progeny of the stated cross in August 2008 in a greenhouse in Gilroy, Calif.

The first act of asexual reproduction of 'PEQZ0004' was accomplished when vegetative cuttings were propagated from the initial selection in the August 2008 in a greenhouse in Gilroy, Calif.

BRIEF SUMMARY OF INVENTION

Horticultural examination of plants grown from cuttings of the plant initiated in August 2008 in Gilroy, Calif., and continuing thereafter, has demonstrated that the combination of characteristics as herein disclosed for 'PEQZ0004' are firmly fixed and are retained through successive generations of asexual reproduction.

'PEQZ0004' has not been observed under all possible environmental conditions. The phenotype may vary significantly with variations in environment such as temperature, light intensity, and day length.

A Plant Breeder's Right for this cultivar was applied for in Canada on Nov. 1, 2011, No. 11-7415. 'PEQZ0004' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0004' with colors being as true as possible with an illustration of this type.

Figure 1:
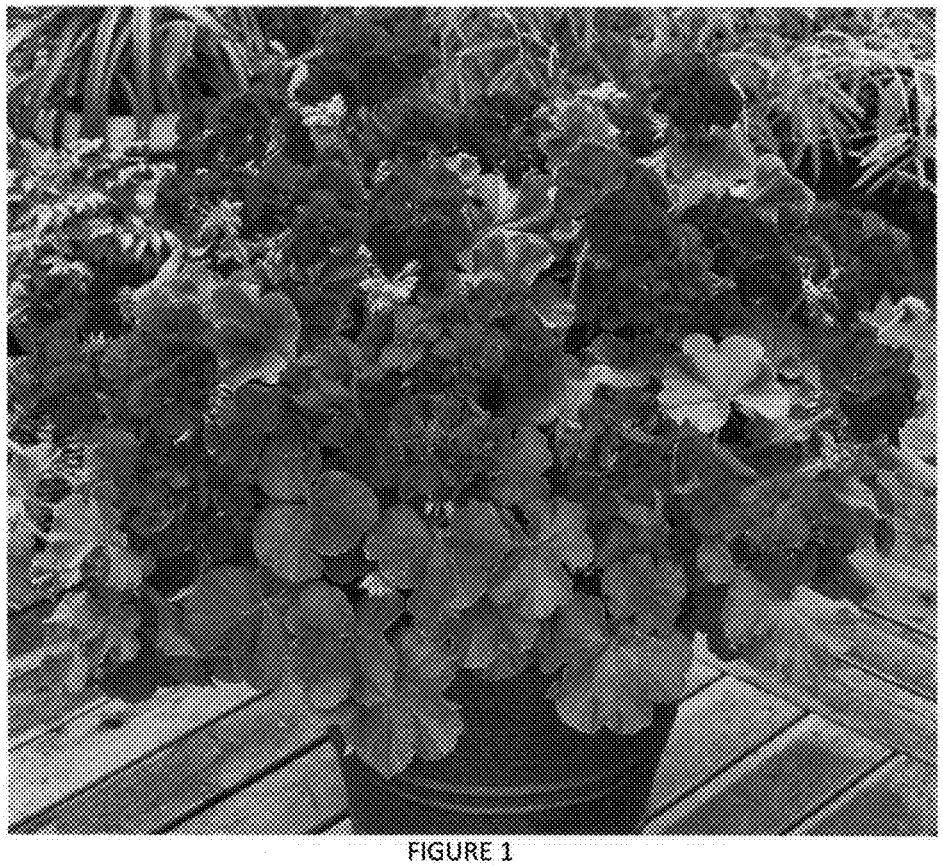
Figure 2:
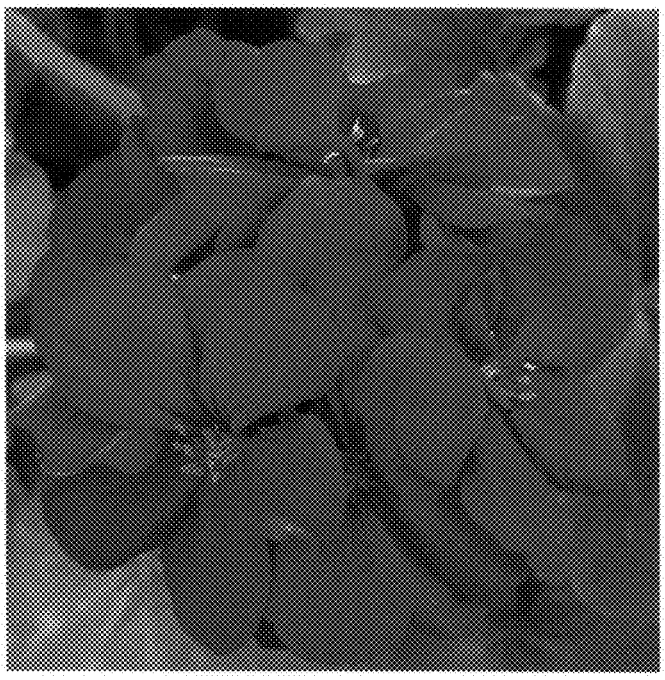

The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. under natural light in late May 2012. These plants were approximately 17-19 weeks old and were grown in a 1 gallon pots, in a greenhouse trial. The plants shown in the photographs were about 25 weeks old growing in a 10 inch pot in a greenhouse. The photographs were taken in April 2012.

Color Chart used: Royal Horticultural Society Colour Chart (R.H.S.) 2001

TABLE 1

DIFFERENCES BETWEEN THE NEW VARIETY 'PEQZ0004' AND A MOST SIMILAR VARIETY

| | 'PEQZ0004' | 'Amri Trared' (U.S. Plant Pat. No. 20,245) |
|---|---|---|
| Flower size: | Smaller | Larger |
| Plant habit size: | Smaller | Larger |
| Flower color: | More blue-red | More darker red |

Plant:

*Form, growth and habit.*—Upright, outwardly spreading and rounded growth habit. Vigorous, well branched and grows well in sun or semi-shade.

*Plant height.*—20-23.0 cm.

*Plant height (inflorescence included).*—27-30.0 cm.

*Plant width.*—45-50.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 146A mottled with some RHS 146B.

*Immature leaf, lower surface.*—Closest to RHS 146A mottled with some RHS 146B.

*Mature leaf, color upper surface.*—Closest to RHS 146A mottled with some RHS 146B.

*Mature leaf, color lower surface.*—Closest to RHS 146A mottled with some RHS 146B.

*Length.*—4.6-6.2 cm.

*Width.*—8.2-11.0 cm.

*Shape.*—Reniform.

*Base shape.*—Cordate.

*Apex shape.*—Mucronulate.

*Margin.*—Dentate.

*Texture upper side.*—Hirsute; sparse pilose.

*Texture lower side.*—Hirsute; sparse pilose.

*Leaf zone.*—Usually absent.

*Color of veins, upper surface.*—RHS 146C.

*Color of veins, lower surface.*—RHS 146C.

*Pattern of veining.*—Palmate.

*Petiole color.*—Between RHS 146B and RHS 146C.

*Petiole length.*—9.5-13.0 cm.

*Diameter of petiole.*—0.3 cm.

*Texture.*—Hirsute; heavily pilose.

Stem:

*Quantity of branches.*—8-10.

*Color of stem.*—RHS 144B.

*Length of stem.*—15-20.0 cm.

*Diameter of stem.*—0.7-0.8 cm.

*Length of internodes.*—1.5-2.0 cm.

*Texture.*—Heavily pilose; hirsute; sparse glandular hairs.

Peduncle:

*Color of peduncle.*—RHS 144A.

*Length of peduncle.*—14-17.5 cm.

*Peduncle diameter.*—0.3-0.4 cm.

*Texture.*—Heavily pilose; hirsute; sparse glandular hairs.

Pedicel:

*Color of pedicel.*—RHS 144B heavily overlaid with anthocyanins of RHS 183C in varying hues or intensities.

*Length of pedicel.*—3.0 cm.

*Diameter of pedicel.*—0.15 cm.

*Texture.*—Pilose; glandular hairs.

Inflorescence:

*Type.*—An umbel, semi-spherical or nearly semi-spherical.

*Lastingness of individual flowers.*—7-9 days at 18° C. temperature.

*Number of inflorescences per plant.*—19-21 umbels with open florets, and 13-15 with only buds.

*Number of flowers per inflorescence.*—Approximately 20-30.

*Flower, self-cleaning.*—No.

*Fragrance.*—None.

*Umbel diameter.*—12-14.0 cm.

*Umbel depth.*—About 7.0 cm.

Bud (just before opening):

*Color.*—Closest to RHS 53A.

*Length.*—1.4-1.6 cm.

*Width.*—0.7-0.9 cm.

*Shape.*—Elliptical.

Corolla:

*Form.*—Semi-double.

*Number of petals.*—5-7.

*Diameter of flower (cm).*—5.3-5.5 cm.

*Depth of flower (cm).*—1.3-1.7 cm.

Upper petals:

*Color upper petals, upper surface.*—Closest to RHS 46A but brighter and more blue-red, more royal velvety looking with a satiny sheen; and veining of RHS 187A.

*Color upper petals, lower surface.*—Closest to RHS 46A but lighter in hue.

*Length of upper petals.*—2.4 cm.

*Width of upper petals.*—1.7 cm.

Lower petals:

*Color lower petals, upper surface.*—Closest to RHS 46A but brighter and more blue-red, more royal velvety looking with a satiny sheen.

*Color lower petals, lower surface.*—Closest to RHS 46A but lighter in hue.

*Length of lower petals.*—2.3-2.7 cm.

*Width of lower petals.*—0.9-2.5 cm.

All petals:

*Petal shape.*—Spatulate.

*Apex shape.*—Rounded.

*Margin.*—Entire.

*Base.*—Cuneate.

*Petal texture.*—Papillose.

*Number of petaloids.*—3-5.

*Color petaloids, upper surface.*—Closest to RHS 46A but brighter and more blue-red, more royal velvety looking with a satiny sheen.

*Lower surface.*—Closest to RHS 46A but lighter in hue.

*Shape.*—Spatulate.

*Average length.*—1.0-1.5 cm.

*Average width.*—0.9-1.1 cm.

Calyx:

*Number of sepals.*—5, in a whorl, fused at the base.

*Color of sepals.*—RHS 144B with lighter margins.

*Length of sepals.*—1.3-1.4 cm.

*Width of sepals*.—0.3-0.4 cm.

*Sepal shape*.—Narrowly lanceolate.

*Apex shape*.—Acute.

*Margins*.—Entire.

*Sepal texture outer surface*.—Long pilose hair with some glandular hairs.

*Inner surface*.—Smooth, glabrous.

Reproductive organs:

*Gynoecium*.—Pistil: 1. Length: 1.0 cm. Style color: Closest to RHS 47B. Style length: 0.5-0.6 cm. Stigma color: Closest to RHS 53B. Ovary color: RHS 144B covered with white hairs. Ovary length: 0.5 cm. Ovary diameter: 0.2 cm.

*Androecium*.—Number of anthers: About 12. Length filaments: 0.5 cm. Color of filaments: RHS N 155C basally with RHS N57A. upper and a RHS 60B to RHS 60C apex. Length of anthers: 0.2 cm. Anther color: Closest to RHS 47B. Color of pollen: RHS N25B. Pollen amount: Normal. Fertility/seed set: No seed set observed. Disease/pest resistance: Has not been observed to date.

What is claimed is:

1. A new and distinct variety of *Pelargonium* plant named 'PEQZ0004' substantially as illustrated and described herein.

* * * * *